United States Patent
Hohmann et al.

(10) Patent No.: US 11,504,448 B2
(45) Date of Patent: Nov. 22, 2022

(54) HIGH-IMPACT, TRANSPARENT PROSTHESIS MATERIAL HAVING A LOW RESIDUAL MMA CONTENT

(71) Applicant: KULZER GMBH, Hanau (DE)

(72) Inventors: Alfred Hohmann, Schmitten (DE); Susanne Busch, Wehrheim (DE)

(73) Assignee: KULZER GMBH, Hanau (DE)

( * ) Notice: Subject to any disclaimer, the term of this patent is extended or adjusted under 35 U.S.C. 154(b) by 1220 days.

(21) Appl. No.: 15/775,453

(22) PCT Filed: Nov. 11, 2016

(86) PCT No.: PCT/EP2016/077420
§ 371 (c)(1),
(2) Date: May 11, 2018

(87) PCT Pub. No.: WO2017/081244
PCT Pub. Date: May 18, 2017

(65) Prior Publication Data
US 2020/0289705 A1 Sep. 17, 2020

(30) Foreign Application Priority Data
Nov. 12, 2015 (DE) .............. 10 2015 119 539.9

(51) Int. Cl.
    C08L 33/12   (2006.01)
    C08L 33/14   (2006.01)
    C08L 75/04   (2006.01)
    A61L 27/48   (2006.01)
    A61L 27/26   (2006.01)

(52) U.S. Cl.
    CPC .............. *A61L 27/26* (2013.01); *A61L 27/48* (2013.01); *C08L 33/12* (2013.01); *C08L 33/14* (2013.01); *C08L 75/04* (2013.01); *A61L 2430/12* (2013.01)

(58) Field of Classification Search
    CPC ........ A61L 27/26; A61L 27/48; A61L 24/043; A61L 24/0094; C08L 33/12; C08L 33/14; C08L 75/04
    See application file for complete search history.

(56) References Cited

U.S. PATENT DOCUMENTS

| | | |
|---|---|---|
| 9,795,541 B2 | 10/2017 | Fontein et al. |
| 2005/0124762 A1 | 6/2005 | Cohen et al. |
| 2006/0217488 A1 * | 9/2006 | Renz .............. A61L 27/14 525/70 |
| 2010/0307378 A1 * | 12/2010 | Trujillo-Lemon .... C07C 271/24 106/35 |
| 2011/0269894 A1 | 11/2011 | Miyamoto |
| 2012/0309864 A1 * | 12/2012 | Ruppert ............. A01L 15/00 525/256 |
| 2015/0231041 A1 | 8/2015 | Bublewitz et al. |
| 2016/0128909 A1 | 5/2016 | Fontein et al. |
| 2017/0151368 A1 * | 6/2017 | Ruppert ............. A61L 27/50 |
| 2017/0156990 A1 | 6/2017 | Ruppert et al. |
| 2017/0340773 A9 | 11/2017 | Ruppert et al. |

FOREIGN PATENT DOCUMENTS

| | | |
|---|---|---|
| EP | 1 702 633 A2 | 9/2006 |
| EP | 2 529 762 A2 | 12/2012 |
| EP | 3 020 361 A1 | 5/2016 |
| EP | 3072498 A1 * | 9/2016 |
| WO | 2010/051793 A1 | 5/2010 |
| WO | 2016/001236 A1 | 1/2016 |
| WO | 2016/001242 A1 | 1/2016 |

OTHER PUBLICATIONS

Husár et al; Chem. Soc. Rev., 2012, 41, pp. 2395-2405. (Year: 2012).*
Database CA—Chemical Abstracts XP00276720; Culbertson et al. "Acryloyloxyalkyl carbamates: synthesis, characterization and some potential uses", Organic Coatings and Plastic Chemistry (1979).
Anonymous: CAS # 63225-53-6; "2-[[Butylamino)carbonyl]oxy]ethyl acrylate, Ebecryl 1029 . . . ", 1 Hanuary 2017, XP055344643, Retrieved from the internet:URL:http://www.chemblink.com/products/6322 5-53-6.htm.
International Search Report dated Mar. 1, 2017.

* cited by examiner

*Primary Examiner* — Karuna P Reddy
(74) *Attorney, Agent, or Firm* — Norris McLaughlin, P.A.

(57) ABSTRACT

The subject matter of the invention is an autopolymerisable 2-component prosthetic base material, a kit containing the material as well as a method for its production comprising at least one liquid monomer component (A), and at least one powdered component (B), wherein the prosthetic material in component (A) besides methylmethacrylate contains at least one N-alkyl-substituted acryloyloxy carbamate having a molecular mass of less than or equal to 250 g/mol, optionally at least one at least di-functional urethane (meth)acrylate, a di-, tri-, tetra- or multi-functional monomer not being urethane (meth)acrylate, and optionally polymeric particles having a primary particle size of less than 800 nm, and the powdered component (B) comprises polymeric particles having at least three different particle size fractions, and both (A) and (B) contains at least one initiator or at least one component of an initiator system for autopolymerisation.

18 Claims, No Drawings

HIGH-IMPACT, TRANSPARENT PROSTHESIS MATERIAL HAVING A LOW RESIDUAL MMA CONTENT

This application is a 371 of International Patent Application No. PCT/EP2016/077420, filed Nov. 11, 2016, which claims foreign priority benefit under 35 U.S.C. § 119 of the German Patent Application No. 10 2015 119 539.9, filed Nov. 12, 2015, the disclosures of which are incorporated herein by reference.

The subject matter of the invention is an autopolymerisable 2-component prosthetic base material, a kit containing the material as well as a method for its production comprising at least one liquid monomer component (A), and at least one powdered component (B), wherein the prosthetic material in component (A) besides methylmethacrylate contains at least one N-alkyl-substituted acryloyloxy carbamate having a molecular mass of less than or equal to 250 g/mol, optionally at least one at least di-functional urethane (meth)acrylate, a di-, tri-, tetra- or multi-functional monomer not being urethane (meth)acrylate, and optionally polymeric particles having a primary particle size of less than 800 nm, and the powdered component (B) comprises polymeric particles having at least three different particle size fractions, and both (A) and (B) contains at least one initiator or at least one component of an initiator system for autopolymerisation.

Autopolymerisable prosthetic base materials, also referred to as cold-curing prosthetic base materials have the advantage of an easy and fast processing in comparison with hot-curing systems. However, the polymerised prosthetic base materials contain a higher residual methylmethacrylate (MMA) content in the first days after production. The norm for cold-curing prosthetic base materials allows up to 4.5% by weight of residual MMA content 48 hours after production. Despite this restriction, patients are always allergic to their prosthesis.

PalaXpressUltra has a heightened fracture toughness, but below the standard values. This material contains a residual MMA content of 2.9% by weight and has a medium transparency of less than 85% only. For example, the SR Ivocap system is provided from Ivoclar, which has high-impact properties and shall have a residual MMA content of 2.2% by weight. However, this is a hot-polymerisate. The relevant norm requires a maximum content of 3% by weight residual MMA content for hot-polymerisates. A disadvantage of this system is the necessity to incur a high purchase price for the Ivobase-system without which the Ivocaps may not be usefully processed. Furthermore, cold-curing prosthesis materials exist having very high transparency, such as Pala Xpress. It has a residual MMA content of 3.3% by weight, wherein it does not however have an heightened fracture resistance.

There is a need to have a prosthesis material which tolerates brief loads, such as the afore-mentioned brief, high mechanical loads, without the material getting damaged, with the concurrent advantages of a autopolymerised plastic. These prosthesis materials are referred to as cold-curing high-impact materials. Requirements for these materials are described in DIN ISO 20795-1. High-impact materials have been on the market for several years, but are all members of the group of hot-curing prosthesis materials.

It was the object of the invention to provide a material, in particular a material being suitable in the medical field, preferably a prosthetic base material for cold-polymerisation, which meets and preferably exceeds the standards of norm DIN ISO 20795-1 concerning fracture toughness. In addition, the material shall have a clearly improved transparency. It was a further object to obtain a very low residual MMA content in the polymerised material in regards to a cold-polymerisate. Furthermore, it was the object for the material to be producible without elaborate additional devices, in particular processing without special additional devices shall also be possible. The material shall to be processed with typical dental technology techniques and devices. It was a further object to provide a high-fracture tough material, in particular a prosthesis material having very high transparency.

It has surprisingly been found that, with the 2-component prosthetic base material obtainable by mixing and polymerising under the terms of a cold-polymerisation or autopolymerisation, respectively, of component (A) and component (B), a material is obtainable which combines a very high transparency, high fracture toughness and a low residual MMA content (residual methylmethacrylate content) in a single material and may nevertheless by processed easily corresponding to a cold-curing plastic.

The subject matter of the invention is a polymerisable prosthetic base material having a residual monomer content, according to norm ISO 20795-1:2013 of a maximum of 2.2% by weight, a fracture toughness expressed as maximum factor of the stress intensity of greater than/equal to 2 $MPa/m^2$ and a total fracture work of greater than or equal to 1200 $J/m^2$, which additionally has a very high transparency of greater than 90%. Due to the high transparency, the material is also suitable for e.g. occlusal splints and surgical guides for implant works.

The object of the invention is an autopolymerisable 2-component prosthetic base material, in particular obtainable by mixing at least one liquid monomer component (A) and polymerisation under the terms of autopolymerisation, and at least one powdered component (B), wherein the prosthetic base material comprises at least one liquid monomer component (A) and at least one powdered component (B), wherein component (A) comprises (i) at least one methylmethacrylate as well as, optionally, at least one (2-alkyl) acrylic acid ester not being methylmethacrylate,
(ii) at least one N-alkyl or N-alkenyl-substituted acryloyloxy carbamate having a molecular mass of less than or equal to 250 g/mol,
(iii) optionally, at least one at least di-functional urethane (meth)acrylate,
(iv) at least one di-, tri, tetra- or multi-functional monomer not being urethane (meth)acrylate,
(v) optionally, polymeric particles having a primary particle size of less than 800 nm, in particular core-shell particles, in particular having a primary particle size of 500 nm to 10 nm,
(vi) at least one initiator or at least one component of an initiator system for autopolymerisation, and
component (B) comprises
(i) at least one powdered component of polymeric particles comprising at least three different fractions of particle sizes of polymeric particles, in particular the average particle size of each fraction of the at least three fractions of particle sizes is at least 5 micrometers apart from the average particle size of the other two fractions, and preferably the average particle sizes of all fractions are in the range of 10 to 120 micrometers, in particular of 30 to 65 micrometer, preferably the three fractions are selected
1) from polymeric particles of an average particle size
 a) of 25 to less than 40 µm, in particular 30 to less than 40 µm, preferably 35 µm with plus/minus 2.5 µm b) of 40 to less than 55 µm, in particular of 40 to 50 µm, preferably 45 µm with plus/minus 2.5 µm c) of 55 to 100 µm, in particular 55 to 80 µm, preferably 55 to 65 µm, more preferably 60 µm with plus/minus 2.5 µm, or preferably 2) from polymeric particles of an average particle size a) of 35 µm with plus/minus 2.5 µm b) of 45 µm with plus/minus 2.5 µm c) of 60 µm with plus/minus 2.5 µm, wherein the weight ration of a) to b) to c) is from 12 to 18 to 1 to 1 to 5, preferably from 14 to 17 to 1 to 2 to 4, particularly preferably from 15 to 16 to 1 to 3 having a total variability of the present value of +/−0.05% by weight, as well as (ii) at least one initiator or at least one component of an initiator system for autopolymerisation.

In order to reduce the residual monomer content of MMA according to the invention, for one thing exchange of the MMA by other components is possible, and optionally increase of the degree of polymerisation by a suitable temperature control also. Temperature development during polymerisation is decisively influenced by the initiator system, the monomer system and the polymer beads used. These components must be suitably matched to each other. Strong temperature development in the course of polymerisation usually results in a higher degree of polymerisation and high flexural strength, but at the expense of fitting accuracy, because the shrinkage is very high, and at the expense of fracture toughness. Moreover, air bubbles may occur in the product. On the other side, if the temperature is too low during polymerisation, it may adversely affect the transparency and robustness. Further, usual polymerisation times are not sufficient in this case for achieving the final hardness of the material and the required residual MMA content in accordance with the norm mentioned above. The mechanical properties are additionally influenced by selection of the right polymer beads differing besides the chemical composition in the average particle size and the degree of cross-linking of the beads. Ideally, the powder component comprises large beads yielding good mechanical properties in the prosthesis material, medium beads providing the system with its robustness against discolorations, as well as an amount of small beads which may find space in the interstices of the others and increase the packing density. Large beads slightly result in whitening and may therefore only be used in a certain amount. In the case of medium beads, the influence on the system is determined by their swelling behavior. Very small beads usually swell very quickly and very strongly increase the viscosity of the mixed prosthesis material such that the risk increases that a correct flow into the prosthesis mould is no longer guaranteed. Therefore, the ideal diameter of the beads is also bounded below.

High transparency may be achieved by optimal selection of the recipe components relating to their refractive indexes. For solving the aforementioned object, all the components were analysed for their specific influence on the reaction system and combined such that the processing time when mixing the powder component with the selected monomer system is long enough to fill even a double cuvette bubble-freely. At the same time, the temperature development is so high that usual polymerisation times are sufficient and high impact values are achieved despite high flexural strength, the transparency is very good and an outstandingly low residual MMA content results.

The optimal sphere packing for attainment of the mechanical values is achieved by use of a defined trimodal bead system in which the smallest polymeric particles, in particular beads, have an average diameter of approx. 35 micrometers, the medium polymeric particles have an average diameter of approx. 45 micrometers and the largest polymeric particles have a medium diameter of approx. 60 µm. Preferably, the amounts of the three beads, synonymously particle size fractions of polymeric particles are definedly matched to each other. Moreover, the optimal sphere packing in the prosthesis material may be further improved by use of polymeric particles having nanoscale primary particles which preferably are present in the liquid monomer component to be able to set an optimal homogenous distribution. Preferably, at least one particle size fraction comprises core-shell particles to obtain a still higher fracture safety. The MMA-based monomer matrix is preferably modified by at least 5% by weight, preferably 10% by weight of a short-chain, aliphatic acryloyloxyethyl carbamate.

Surprisingly, reduction of the residual MMA content by at least 30% by weight could be attained due to the exchange of 10% by weight MMA for the carbamate. The product according to the invention only has still 2.0% by weight residual MMA content 48 hours after production in the case of a polymerisation time of 30 min in a pressure pot at 2 bar and a water temperature of 55° C. The value measured decreases to 1.8% by weight after 4 days. Reduction of the MMA content to 1.8% by weight may be accelerated by performing the polymerisation for 60 min. In this case, the value of 1.8% by weight may already be achieved 48 hours after the production. Since the norm for hot-curing materials is far undershot by these values, the material according to the invention, for the first time, no longer has the disadvantage of usual cold-polymerisates having a significantly higher residual MMA content. The known cold-polymerisates have a higher residual MMA content i.a. due to the short polymerisation time and the mild polymerisation conditions.

The prosthetic base material according to the invention has a residual MMA content being by at least 30% by weight lower than classical cold-polymerisates, and has a fracture work value of at least 1200 $J/m^2$ and a flexural strength value of at least 70 MPa, as well as a fracture stability being far superior to classical cold-polymerisates. At the same time, the transparency preferably is at least 95%.

It has surprisingly been found that the residual monomer content of methylmethacrylate in the polymerised material according to norm conditions may further be clearly reduced of the content if at least one (ii) N-alkyl or N-alkenyl-substituted acryloyloxy carbamate having a molecular mass of less than or equal to 250 g/mol or a mixture of carbamates is used in the composition and the amount of carbamate approximately substitutes at least the same amount of methylmethacrylate. In this context, a N-alkyl or N-alkenyl-substituted acryloyloxy alkylene carbamate (N-alkyl-acryloyloxy-$(CH_2)_n$-carbamate, n=1, 2, 3, 4, 5, 6) is preferably used as N-alkyl or N-alkenyl-substituted acryloyloxy carbamate, particularly preferably a N-alkyl or N-alkenyl-substituted acryloyloxy methylene carbamate, acryloyloxy ethylene carbamate or acryloyloxy propylene carbamate. N-alkylene acryloyloxy ethylene carbamate is particularly preferred. More preferably, the N-alkyl-substituted acryloyloxy carbamate is selected from methyl-, ethyl-, n-propyl-, iso-propyl-, n-butyl-, i-butyl-, tert.-butyl-, Pentyl- or hexyl- and their structural isomers. Preferred carbamates are: iso-butyl acryloyloxyethyl carbamate, tert.-butyl acryloyloxyethyl carbamate, n-propyl acryloyloxyethyl carbamate, n-propyl acryloyloxypropyl carbamate, wherein n-butyl acryloyloxyethyl carbamate (BAEC) may be used according to the invention. Another subject matter of the invention is the use of core-shell particles modified by at least one elastic phase and of at least one N-alkyl or N-alkenyl-substituted carbamate having a molecular mass of less than or equal to 250 g/mol, preferably of a mono-carbamate.

Preferably, a monomer component having a MMA content between 60 to 95% by weight, preferably of 60 to 90% by weight, particularly preferably of 60 to 85% by weight or also 70 to 90% by weight, and a content of 5 to 20% by weight of an aliphatic acryloyloxy carbamate having a molecular mass of less than 250 g/mol is used. In addition, a mixture of polymeric particles having at least three different particle size fractions of PMMA-based polymeric particles or beads, respectively, differing from one another in their average diameter by at least 5 µm, are preferably used.

According to a particularly preferred alternative, the prosthetic base material comprises components (A) and (B), wherein the prosthetic base material comprises in the total composition in percent by weight ad 100% by weight:
(i) 20 to 50% by weight methylmethacrylate (MMA),
(ii) 1 to 30% by weight at least one N-alkyl- or N-alkenyl-substituted acryloyloxy carbamate having a molecular mass of less than or equal to 250 g/mol,
(iii) 0.5 to 10% by weight at least one at least di-functional urethane (meth)acrylate, such as oligomer or dendrimer,
(iv) 0.05 to 10% at least one di-, tri, tetra- or multi-functional monomer not being urethane (meth)acrylate,
(v) 0.1 to 10% by weight polymeric particles being present as core-shell particles modified by an elastic phase, having a primary particle size of less than 800 nm,
(vi) 0.05 to 2% by weight at least one initiator or at least one component of an initiator system for autopolymerisation, as well as
(vii) 48.3 to 78.3% by weight, in particular 55 to 65% by weight, at least one powdered component (B) containing polymeric particles comprising at least three different fractions of particle sizes of polymeric particles, wherein the information in % by weight is based on the total composition, and wherein the three fractions are selected from polymeric particles of an average particle size a) of 25 to less than 40 µm, being present at 50 to 90% by weight,
b) of 40 to less than 55 µm, being present at 0.1 to 20% by weight, and c) of 55 to 100 µm, being present at 0.5 to 30% by weight, wherein the information in % by weight of a), b) and c) are based on the total composition of component (B).

Likewise, a subject matter of the invention is a polymerised prosthetic base material having a residual monomer content of MMA of less than or equal to 3% by weight determined according to ISO 20795-1:2013, in particular it has a residual monomer content of MMA of less than or equal to 2.5% by weight, preferably of less than or equal to 2.4, 2.3, 2.2, 2.1, 2.05, 2.0 or 1.9% by weight, in particular having total variability of the present value of +/−0.05% by weight.

Furthermore, a subject matter of the invention is a polymerised prosthetic base material having a transparency of greater than or equal to 95% (measured against colour test bodies produced in metal moulds having a thickness of 3 mm by means of colorimeter SF 600 (Datacolor)), in particular greater than or equal to 97%.

According to a further alternative, a subject matter of the invention is a polymerised prosthetic base material having a fracture toughness as maximum factor of the stress intensity $K_{max}$ of $\geq 2.4$ Mpa·m$^{1/2}$, in particular greater than or equal to 2.45 Mpa·m$^{1/2}$, preferably greater than or equal to 2.5 Mpa·m$^{1/2}$, and fracture toughness as total fracture work $W_f$ (J/m$^2$) of $\geq 1000$ J/m$^2$, in particular of greater than or equal to 1100 J/m$^2$, more preferably of greater than or equal to 1250 J/m$^2$. Particularly preferably, the flexural strength is additionally greater than 65 MPa, particularly preferably greater than 70 Mpa. more preferably greater than 75 Mpa. Further, it is preferred for the transparency of the unpigmented, polymerised prostheses to be in the range of greater than or equal to 90%, in particular of greater than or equal to 95% (measured against plates having a thickness of 3 mm).

According to the invention, the objects are met by synergistical use of the carbamate having a molecular weight of less than or equal to 250 g/mol, the use of at least one or more fractions of core-shell particles having an elastic core, as well as of at least three different fractions of particles sizes of the polymeric particles in the powdered component. The selection of specific core-shell particles having a refractive index similar to that of the polymerised prosthetic material ensured high transparency of the prosthesis material. Therefore, the polymeric particles having a particle size of less than 800 nm are preferably present as core-shell particles modified by an elastic phase and preferably have a refractive index of about 1.49 (R.I.~1.4900).

Particularly preferred core-shell particles according to the invention are present in aggregated form. The objects may be met by use of aggregated core-shell particles (irregularly shaped aggregates, $d_{50}$~50-300 µm), the primary particle size is approx. 200-400 nm. Probably, the core-shell particles are present in aggregated form due to surface interaction in the solid. The additive is mixed with the liquid and forms a stable suspension that just weakly sediments within a few weeks. As a result of suspending in MMA, the aggregates relatively quickly degrade into the primary particles.

Due to the use of core-shell particles as a high-impact additive in conjunction with at least one carbamate having a molecular weight of less than 250 g/mol, preferably n-butyl acryloxyethyl carbamate, it is possible to produce prosthesis materials meeting the requirements concerning high-impact properties of ISO 20795-1. In addition, a prosthesis material may be provided having its flexural strength and E-modulus in the same order as non-high-impact materials and at the same time being highly transparent and colour-stable. The prostheses according to the invention do not show any whitening by contact with water-containing materials, such as e.g. duplicating gels or plasters, during and after the polymerisation process.

Another subject matter of the invention is a prosthetic base material which, each independently, comprises component (A), which contains (v) polymeric particles being present as core-shell particles modified by an elastic phase, and in particular the elastic phase comprises styrene-butyl acrylate polymer, and/or, independently, component (B) comprises at least one fraction of polymeric particles being present as core-shell particles modified by an elastic phase, wherein the elastic phase is present as core in harder shell (core-shell particles, and in particular the elastic phase comprises styrene-butyl acrylate polymer. The core-shell particles usually comprise (irregularly shaped aggregates, $d_{50}$~50-300 µm) being solved into primary particles in the monomer component. The primary particle size is approx. 200-400 nm. Probably, the core-shell particles are present in aggregated form due to surface interaction in the solid.

Furthermore, the prosthesis material according to the invention may be mixed and processed with usual dental technology methods and instruments. Conventional techniques and tools known by the dental technician may be used for processing. Special investment materials, plasters, cuvettes, devices etc. (such as e.g. in the Ivoclar system) may be avoided.

In order to distinguish prosthesis materials from usual dental materials, it is emphasized that prosthesis materials comprise substantial amounts of polymeric powdered components, such as PMMA (Poly(meth)methylacrylate) and/or (Poly(ethyl)methacrylate), in particular of greater than or equal to 50% by weight in the total composition. Usual prosthetic materials are usually provided in a kit having a powdered component and a liquid component. Dental materials for the production of fillings are largely based on inorganic fillers (dental glasses) preferably being present in an amount of greater than 60% by weight in the polymerisable compositions as well as mainly high-molecular monomers being based on BisGMA (Bisphenol-A-(di)methacrylate).

The at least one di-functional or multi-functional urethane (meth)acrylate may be selected from an urethane dimethacrylate, preferably a bis(methacryloxy-2-ethoxycabonylamino) alkylene, acryloxy-substituted urethane dendrimer, diurethane acrylate oligomer, urethane (meth) acrylate dendrimers, urethane methacrylate polymer approx. 300 g/mol (Dendrimer, Laromer UA9049, 50% in acrylate monoblend (41.7% by weight HEMA-TMDI/8% by weight TEGDMA, cas. no. 109-16-0), alkyl-functional urethane dimethacrylate oligomers, aromatic-functionalised urethane dimethacrylate oligomers, aliphatic unsaturated urethane acrylates, bis(methacryloxy-2-ethoxycarbonylamino)-substituted polyether, aromatic urethane diacrylate oligomers, aliphatic urethane diacrylate oligomers, mono-functional urethane diacrylates, aliphatic urethan diacrylates, hexafunctional urethane resins, aliphatic urethane triacrylates, UDMA, aliphatic urethance acrylate oligomers, unsaturated aliphatic urethane acrylates. Suitable urethane (meth)acrylates are available under the following brand names: Ebecryl 230 (aliphatic urethane diacrylate), Actilane 9290, Craynor 9200 (Diurethane acrylate oligomer), Ebecryl 210 (aromatic urethane diacrylate oligomers), Ebecryl 270 (aliphatic urethane diacrylate oligomers), Actilane 165, Actilane 250, Genomer 1122 (monofunctional urethane acrylate), Photomer 6210 (cas no. 52404-33-8, aliphatic urethane diacrylate), Photomer 6623 (hexa-functional aliphatic urethane resin), Photomer 6891 (aliphatic urethane triacrylate), UDMA, Roskydal LS 2258 (aliphatic urethane acrylate oligomer), Roskydal XP 2513 (unsaturated aliphatic urethane acrylate).

In this context, it is particularly preferred for component (v), the core-shell particles modified by at least one elastic phase, to be present at 0.001 to 20% by weight, in particular up to 10% by weight, preferably up to 5% by weight, based on the total composition of component (A), and for (ii) at least one carbamate having a molecular mass of less than 250 g/mol, in particular no di-urethane, to be present at 0.001 to 30% by weight, in particular up to 10% by weight, more preferably up to 5% by weight, based on the total composition of component (A) (i.e. on 100% by weight of component (A)). The core-shell particles are also referred to as high-impact modifiers.

The prosthetic base material according to the invention passes the Suntest according to ISO 20795-1 despite the added high-impact modifier (core-shell particles) and the carbamate.

Particularly preferred prosthetic base materials preferably have core-shell particles, in which the distribution of the elastic phase of the modified core-shell particles is selected from possibilities a to d: a) elastic phase as core (e.g. made of butylacrylate) in solid outer shell (e.g. made of PMMA) (core-shell particles); b) multiple elastic phases as cores in a solid matrix; c) core-shell particles from a), distributed in solid matrix, and d) solid core with elastic phase as outer shell. Core-shell particles according to the invention may also have the following multi-layer structure, e) an inlying core with multiple layers as shells and one outer shell, wherein in particular (i) at least one of the shells, preferably the outer shell, is solid and the remaining shells and the core, each independently, consists of elastic phases. In alternatives, the elastic phases and the solid phases may be otherwise divided between the shells and the core.

Furthermore, preferred core-shell particles have a refractive index similar to that of the polymerised prosthesis material. Preferably, the refractive index of the core-shell particles is about 1.49 having a total variability of the present value of plus/minus 0.02, in particular +/−0.01. According to the invention, particularly preferred core-shell particles are present in aggregated form. In this context, the aggregates of the core-shell particles, which may be randomly shaped, have an average diameter of $d_{50}$~50-300 µm as being an irregularly shaped aggregate. The preferred size of the primary particle size is less than 500 nm, in particular up to 100 nm, preferably from 200 to 400 nm. Core-shell particles having a primary particle size of less than or equal to 200 nm to 2 nm, as well as between 150 to 10 nm may be used as core-shell particles as well.

Preferably, the core-shell particles have a refractive index of 1.48 to 1.60, in particular of 1.49 to 1.55. Particularly preferably, the refractive index of the core-shell particles is in the range of the refractive index of PMMA, preferably the refractive index is therefore about 1.48 to 1.50.

Core-shell particles whose density is 0.9 to 1.5 g/ml, in particular 0.95 to 1.4 g/ml are preferred as well. Preferably, the bulk density is 0.1 to 0.6 g/m at the same time.

A solid outer shell, solid matrix, solid core shall be understood to mean a material, which preferably has a lower elasticity than the material of the elastic phase. Preferred inorganic solid cores show substantially no deformation under the influence of a force, while the organic solid materials undergo an appreciably lower deformation under the influence of a force than the elastic phase. The solid materials as being a solid outer shell, solid matrix and/or solid core stabilize the elastic phase in its shape. An elastic phase is formed by at least one elastic material, which undergoes a reversible deformation under the influence of a force. The deformation of the elastic phase advantageously is fully reversible without force effect.

Preferred components B) preferably comprise at least one powdered component comprising a) polymeric particles comprising polymers in the form of polymer powder comprising polyalkyl(meth)acrylates, optionally being cross-linked and being present as homopolymer or copolymer, wherein the polymers are based on at least one monomer comprising a (meth)acrylat group, selected from methylmethacrylate, ethylmethacrylate, propylmethacrylate, butylmethacrylate, n-hexylmethacrylate, 2-phenoxyethylmethacrylate, isobornylmethacrylate, isodecylmethacrylate, polypropylene glycol monomethacrylate, tetrahydrofurylmethacrylate, methylacrylate, ethylacrylate, propylacrylate, butylacrylate, n-hexylacrylate, 2-phenoxyethylacrylate, isobornylacrylate, isodecylacrylate, polypropylene glycol monoacrylate, tetrahydrofurylacrylate, hydroxyethylacrylate, hydroxypropylacrylate, hydroxyethylmethacrylate, hydroxypropylmethacrylate, a mixture containing at least one of these (meth)acrylates and/or copolymers comprising one or at least two of the aforementioned monomers, polyamide particles, polyamide fibers. In addition, the polymeric particles may also comprise mixtures of dental monomers, such as e.g. MMA and additionally at least one crosslinker.

According to a preferred embodiment variant of the invention, one particle size fraction of polymeric particles of the powdered component (B) comprises, each independently, polymethylmethacrylate (PMMA) particles or beads, respectively. Particularly preferably, the powdered component comprises polymethylmethacrylate (PMMA) beads as polymeric particles and/or splitter polymerisates, in particular having particle sizes of 10-100 µm, and/or is based on copolymers comprising as comonomers, being polymerised into the copolymer, styrene, alpha-methylstyrene, vinyltoluene, substituted vinyltoluene, such as vinylbenzylchloride, vinylhalogenide, such as vinylchloride, vinylester, such as vinylacetate, heterocyclic vinyl compounds, such as 2-vinylpyridine, vinylacetate and vinylpropionate, butadiene, isobutylene, 2-chlorobutadiene, 2-methylbutadiene, vinylpyridine, cyclopentene, (meth)acrylic acid ester, such as methylmethacrylate, ethyl methacrylate, butylmethacrylate, butylacrylate and hydroxyethylmethycrylate, moreover acrylonitrile, maleic acid and maleic acid derivatives, such as, for example, maleic acid anhydride, fumaric acid and fumaric acid derivatives, such as fumaric acid esters, acrylic acid, methacrylic acid, as well as acryl(meth)acrylates, such as benzylmethacrylate or phenylmethacrylate, as well as, optionally, mixtures of these comonomers, and optionally additionally b) inorganic fillers comprising pyrogenic or precipitated silicas, dental glasses, such as aluminosilicate glasses or fluoroaluminosilicate glasses, bariumaluminium silicate, strontium silicate, strontium borosilicate, lithium silicate, lithiumaluminium silicate, phyllosilicates, zeolites, amorphous spherical fillers based on oxide or mixed oxide, in particular mixed oxides of $SiO_2$ and $ZrO_2$, glass fibres and/or carbon fibers, as well as mixtures comprising the powdered components a) and b).

The b) inorganic fillers are usually used in amounts of 0 to 10% by weight, preferably of 0.0001 to 3% by weight, based on the total prosthetic plastic composition or the sum of components (A) and (B), respectively. In component (B) they are usually present in the range of 0 to 20% by weight, preferably of 0.001 to 10% by weight, based on the total composition of component (B) of 100% by weight.

Polymeric particles, which are based on at least one (meth)acrylate monomer having just one (meth)acrylate group or which are based on the mixture of at least two of these (meth)acrylate monomers are in the scope of the invention as well.

Core-shell particles according to the invention preferably comprise as elastic phase at least one poly-(n-butyl acrylate) PBA, particularly preferably styrene-butyl acrylate polymers. Other butadiene-styrene copolymers, nitrile-butadiene copolymers, silicon rubber-(graft copolymerisates), polyurethane polymerisates, polyolefin-based polyurethane (polybutadiene-based polyurethane), which may preferably be present in MMA, are suitable as well. The particle size of the core-shell particles may be less than or equal to 500 nm, such as between 50 nm to 500 nm, in particular less than or equal to 400 nm to 100 nm, or, alternatively, less than 100 nm to 2 nm, the elastic phase may also be based on polydimethylsiloxane-modified polyurethanes and/or epoxy-functionalised elastic phases.

Core-shell particles according to the invention comprise as solid shell, solid core and/or solid matrix at least one (meth)acrylate polymer, preferably one alkyl(meth)acrylate polymer, such as PMMA, polystyrene, an epoxy-functionalised core, as well as homo- or co-condensates of the aforementioned polymers.

Preferred core-shell particles comprise aggregates having $d_{50}$<400 µm and primary particle sizes of $d_{50}$ less than 500 nm. More preferably, the primary particles of the core-shell particles may be greater than or equal to 100 nm, in particular as $d_{50}$-value.

Core-shell particles comprising an elastic core comprising acrylate polymers with solid outer shell, in particular having a particle size of less than 1 micrometer, are also suitable. More preferably, the core-shell particles may have groups being reactive against polymerisable monomers, preferably the outer shell is functionalised by (meth)acrylate groups.

Furthermore, a subject matter of the invention is a prosthetic base material comprising a (A) liquid monomer component, which comprises at least one monomer, in particular a mixture of monomers of methylmethacrylate as well as, optionally, at least one (2-alkyl) acrylic acid ester, in particular component (A) comprises methylmethacrylate. In an alternative, component (A) may contain at least one of the following monomers or a mixture comprising at least two of the mentioned monomers: methylmethacrylate as well as optionally additionally ethylmethacrylate, propyl methacrylate, butylmethacrylate, n-hexylmethacrylate, 2-phenoxyethylmethacrylate, isobornylmethacrylate, isodecylmethacrylate, polypropylene glycol monomethacrylate, tetrahydrofurylmethacrylate, methylacrylate, ethylacrylate, propylacrylate, butylacrylate, n-hexylacrylate, 2-phenoxyethylacrylate, isobornylacrylate, isodecylacrylate, polypropylene glycol monoacrylate, tetrahydrofurylacrylate, hydroxyethylacrylate, hydroxypropylacrylate, hydroxyethylmethacrylate, hydroxypropylmethacrylate, benzyl-, furfuryl- or phenyl-(meth)acrylate, a mixture containing at least one of these (meth)acrylates and/or copolymers comprising one or at least two of the aforementioned monomers.

Furthermore, component (A) comprises at least one (iv) di-, tri-, tetra- or multi-functional monomer not being urethane (meth)acrylate, such as preferably tris-(2-hydroxyethyl) isocyanurate triacrylate (Sartomer 368). Alternatively, one of the following monomers or a mixture comprising at least two of the mentioned monomers may be used as (iv) di-, tri-, tetra- or multi-functional monomer not being urethane (meth)acrylate: 1,4-butandiol dimethacrylate (1,4-BDMA) or pentaerythritol tetraacrylate, bis-GMA monomer (bisphenol-A-glycidylmethacrylate), triethylene glycol dimethacrylate (TEGDMA) and diethylene glycol dimethacrylate (DEGMA), tetraethylene glycol di(meth)acrylate, decanediol di(meth)acrylate, dodecandiol di(meth)acrylate, hexyldexandiol di(meth)acrylate, trimethylolpropane tri(meth)acrylate, pentaerythritol tetra(meth)acrylate, as well as butanediol di(meth)acrylate, ethylene glycol di(meth) acrylate, polyethylene glycol di(meth)acrylate, ethoxylated/propoxylated bisphenol-A-di(meth)acrylate, a mixture comprising at least one of these (meth)acrylates and/or copolymers comprising one or at least two of the aforementioned monomers. Suitable alkylmethacrylates for the liquid component (A) are methyl-, ethyl-, n-propyl-, i-propyl-, n-butyl-, t-butyl-, i-butyl-, benzyl- and furfurylmethacrylate or mixtures thereof. Of these, methylmethacrylate is particularly preferred.

Preferably, the (A) liquid monomer component comprises (i) 60 to 90% by weight, preferably 60 to 85% by weight, methylmethacrylate as well as, optionally, at least one (2-alkyl) acrylic acid ester not being methylmethacrylate, (ii) 5 to 20% by weight at least one N-alkyl- or N-alkenyl-substituted acryloyloxy carbamate having a molecular mass of less than or equal to 250 g/mol,
(iii) 0.5 to 10% by weight at least one at least di-function urethan (meth)acrylate,
(iv) 0.05 to 10% by weight at least one di-, tri-, tetra- or multi-functional monomer not being urethan (meth)acrylate,
(v) 0.1 to 10% by weight polymeric particles being present as core-shell particles modified by an elastic phase, having a primary particle size of less than 800 nm,
(vi) 0.05 to 2% by weight at least one initiator or at least one component of an initiator system for autopolymerisation, wherein the above information in % by weight are based on the total composition of component (A).

The core-shell particles are usually suspended in the monomers.

According to the invention, the total composition of the powdered component (B) is composed as follows:
(i) 90 to 99.95% by weight at least one powdered component of polymeric particles comprising at least three different fractions of particle sizes of polymeric particles, wherein the three fractions are selected from polymeric particles of an average particle size
a) of 25 to less than 40 µm, being present at 50 to 90% by weight, b) of 40 to less than 55 µm, being present at 0.1 to 20% by weight, and c) of 55 to 100 µm, being available at 0.5 to 30% by weight, and
(ii) 0.05 to 10% by weight at least one initiator or at least one component of an initiator system for autopolymerisation, wherein the above information in % by weight is based on the total composition of component (B).

The total composition (A) with 100% by weight and the total composition (B) with 100% by weight may be mixed at a weight ration of (A) to (B) of 1 to 20 to 20 to 1, preferably at a weight ratio of (A) to (B) of 1:10 to 10:1, preferably of 5 to 15 to 9 to 8, preferably of 5 to 8 to 8 to 12, preferably at a weight ratio of (A) to (B) of 7 to 10, in particular having a total variability of the present value of plus/minus 1, preferably of 0.5.

In particular, the amount of methylmethacrylate being liquid at room temperature in the mixed, not yet polymerised prosthetic base material according to the invention, in particular comprising components (A) and (B), amounts to 20 to 50% by weight, preferably 30 to 40% by weight.

Furthermore, a subject matter of the invention is a prosthetic base material that preferably additionally comprises in component (A), (B) or in (A) and (B) at least one or more substance(s) from the groups of fillers, pigments, stabilizers, regulators, antimicrobial additives, UV-absorbing agents, thixotroping agents, catalysts and crosslinkers. Rather small amounts of these additives—as of pigments, stabilizers and regulators—are used, e.g. a total of 0.01 to 3.0, in particular 0.01 to 1.0% by weight, based on the total mass of the material. Suitable stabilizers include e.g. hydroquinone monomethylether or 2,6-di-tert.-butyl-4-methylphenol (BHT).

Likewise, a subject matter of the invention is a prosthetic base material that optionally additionally has at least one initiator or at least one initiator system for autopolymerisation, which may be present in the liquid component (A), the powdered component (B) or in (A) and (B) depending on reaction conditions or polymerisation system, respectively.

The following initiators and/or initiator systems for auto- or cold-polymerisation comprise a) at least one initiator, in particular at least one peroxide and/or azo compound, in particular LPO: dilauroylperoxide, BPO: dibenzoylperoxide, t-BPEH: tert-butylper-2-ehtylhexanoate, AIBN: 2,2"-azobis-(isbutyronitrile), DTBP: di-tert-butylperoxide, and, optionally, b) at least one activator, in particular at least one aromatic amine, such as N,N-dimethyl-p-toluidine, N,N dihydroxyethyl-p-toluidine and/or p-dimethylamino-benzoic acid diethylester, or c) at least one initiator system selected from redox systems, in particular a combination selected from dibenzoylperoxide, dilauroylperoxide, and camphorquinone with amines selected from N,N dimethyl-p-toluidine, N,N-dihydroxyethyl-p-toluidine, and p-dimethylamino-benzoic acid diethylester, or a redox system comprising a peroxide, and a reduction agent selected from ascorbic acid, ascorbic acid derivative, barbituric acid or a barbituric acid derivative, sulfinic acid, sulfinic acid derivative, particularly preferred is a redox system comprising (i) barbituric acid or thiobarbituric acid or a barbituric acid derivative or thiobarbituric acid derivative, and (ii) at least one copper salt or copper complex, and (iii) at least one compound having an ionic halogen atom, particularly preferred is a redox system comprising 1-benzyl-5-phenylbarbituric acid, copper acetylacetonate, triazine derivative, toluidine derivative and/or benzyldibutylammoniumchloride. Particularly preferably, the polymerisation in the two-component prosthetic base material is started by a barbituric acid derivative.

Another subject matter of the invention is a method for the production of a polymerised prosthetic base material, as well as a prosthesis material obtainable according to the method, in which components A) at least one liquid monomer component, and B) at least one powdered component are being mixed and subsequently polymerised or cured, respectively. In this case, it is particularly preferred for the monomer component (A) and the powdered component (B) to be mixed at a weight ratio of 1:10 to 10:1, in particular at a weight ratio of 8 to 12 powdered component to 4 to 8 monomer component. Preferably, 7 to 10 component (A) to (B), wherein the total variability of the present value may amount to +/−1, preferably +/−0.05.

Likewise, a subject matter of the invention is a method in which the monomer component (A) and the powdered component (B) are being mixed, and in particular transferred as polymerised prosthetic base material into a negative mould, such as a casting mold, of at least one dental, prosthetic moulded body, such as tooth, occlusal splint, milling blank or milling circular blank, respectively, dental prosthesis, part of prosthesis, surgical guide, implant, mouthguard, joint prosthesis, crown, telescopic prosthesis and telescopic crown, veneer, dental bridge, prosthetic teeth, implant part, abutment, superstructure, orthodontic appliance and instrument, hoof part, and in particular the material is polymerised under elevated pressure, in particular greater than or equal to 2 bar, such as 2.5 to 10 bar, preferably 2 to 4 bar. Preferably, the polymerisation is carried out at a temperature of 35° C. to 60° C., preferably of 45° C. to 60° C., preferably at approximately 55° C. for 20 to 180 minutes, preferably at approximately 55° C. for 30 minutes. IN this case, the polymerisation is carried out under slightly elevated pressure between 1 to 5 bar, in particular at 2 bar.

Mixing of components A) and B) may be carried out according to the invention by means of simple measures known to the dental technician, such as by means of spatula.

According to a further alternative, a subject matter of the invention is a kit comprising an autopolymerisable prosthetic base material, wherein the kit comprises separated components (A) and (B), characterised in that component (A) comprises (i) 60 to 85% by weight methylmethacrylate,
(ii) 5 to 20% by weight at least one N-alkyl- or N-alkenyl-substituted acryloyloxy carbamate having a molecular mass of less than or equal to 250 g/mol,
(iii) 0.5 to 10% by weight at least one at least di-function urethan (meth)acrylate,
(iv) 0.05 to 10% by weight at least one di-, tri-, tetra- or multi-functional monomer not being urethan (meth)acrylate,
(v) 0.1 to 10% by weight polymeric particles being present as core-shell particles modified by an elastic phase, having a primary particle size of less than 800 nm,
(vi) 0.05 to 2% by weight at least one initiator or at least one component of an initiator system for autopolymerisation, wherein the above information in % by weight are based on the total composition of component (A), as well as
component (B) comprises
(i) 90 to 99.95% by weight at least one powdered component of polymeric particles comprising at least three fractions of particles sizes of polymeric particles, wherein the three fractions are selected from polymeric particles of an average particle size
a) of 25 to less than 40 µm, being present at 20 to 90% by weight, preferably at 50 to 90% by weight,
b) of 40 to less than 55 µm, being present at 0.1 to 50% by weight, preferably at 0.1 to 20% by weight, and
c) of 55 to 100 µm, being present at 0.5 to 50% by weight, preferably at 0.5 to 30% by weight, and
(ii) 0.05 to 10% by weight at least one initiator or at least one component of an initiator system for autopolymerisation, wherein the above information in % by weight is based on the total composition of component (B).

Another subject matter of the invention a polymerised prosthetic base material or the use of the prosthetic base material for the production of the following products in the form of a prosthetic moulded body, in human dental field, such as dental prosthetic moulded body, such as tooth, occlusal splint, milling blank or milling circular blank, respectively, dental prosthesis, part of prosthesis, surgical guide, implant, mouthguard, joint prosthesis, crown, telescopic prosthesis and telescopic crown, veneer, dental bridge, prosthetic teeth, abutment, implant part, superstructure, orthodontic appliance and instrument, prosthetic moulded body in the form of bones or parts thereof, prosthetic moulded body in veterinary field, such as hoof part, in particular for hoof repair materials or in medical prosthetics.

Auto- or cold-polymerisable according to the invention shall be understood to mean a prosthetic material meeting the criteria according to ISO 20795-1 (Pt. 3.1). Cold-polymerising plastics shall be understood to mean compositions, which polymerise below 65° C. Preferably, cold-polymerising prosthesis materials may independently cure or polymerise, respectively, in a temperature range of 50° C. to 65° C., preferably of 50° C. to 60° C., more preferably of 50° C. to 55° C., after mixing components (A) and (B). Preferably, the polymerisation is made over 5 to 180 minutes, preferably for 30 to 60 minutes, particularly preferably for 30 minutes. In accordance with the aforementioned norm, polymerisable compositions, which independently cure or polymerise, respectively, above 65° C., are referred to as hot-curing compositions.

The powder component of the two-component prosthetic base material usually comprises a polymeric particle, in particular based on methacrylate, and/or a bead polymerisate based on methacrylate as powdered component. In this field, bead polymerisates are often referred to as powder.

In a preferred embodiment, crosslinkers have been polymerised at least in part into the beads of the first (co)polymerisate and/or into the beads of the second (co) polymerisate. Accordingly, the first and second bead polymers also comprise cross-linked and partly cross-linked bead polymers.

For cross-linking, it is common to resort to multi-functional comonomers or multi-functional oligomers. Aside from di-, tri- and poly-functional (meth)acrylates, graft crosslinkers having at least two different reactive C—C double bonds, for example, alkylmethacrylates and alkylacrylates, as well as aromatic crosslinkers, such as 1,2-divinylbenzene, 1,3-divinylbenzene and 1,4-divinylbenzene, are suitable for this purpose. Amongst the difunctional (meth)acrylates, in particular, the (meth)acrylates of propandiol, butanediol, hexandiol, octandiol, nonandiol, decanediol, and eicosandiol, as well as the di(meth)acrylates of ethylene glycol, triethylene glycol, tetraethylene glycol, dodecaethylene glycol, tetradecanethylene glycol, propylene glycol, dipropylene glycol, and tetradecanpropylene glycol, moreover glycerol di(meth)acrylate, 2,2-bis [(gamma-methacryloxy-beta-oxypropoxy)-phenylpropane], neopentylglycol di(meth)-acrylate, 2,2-(di-methacryloxy-polyethoxy-phenyl) propane having 2 to 10 ethoxy groups per molecule, as well as 1,2-bis(3-methacryloxy-2-hydroxypropoxy)butane, shall be mentioned. Exemplary, multi-functional (meth)acrylates include, e.g. di-, tri- and/or tetra (meth)acrylates, such as 1,4-butandiol dimethacrylate, ethylene glycol dimethacrylate, as well as di- or trivinylic compounds, such as divinylbenzene. The content of said crosslinker molecules in the starting mixture of the bead polymerisate is in the range of 0.1% by weight to 10% by weight, in particular in the range od 0.5% by weight to 5% by weight.

The radical initiator system required for polymerisation is contained in the liquid component (A) and/or the powdered component (B) depending on reaction conditions and polymerisation system, respectively. Pertinent details are known to the person skilled in the art. For example, in base mixtures for cold-polymerisates, the initiator system is mostly present in both components, the liquid component and the powdered component, and is thus combined when mixing said components. Consequently, one initiator component (c) is usually present in the powdered component (B), in particular in the form of (i) barbituric acid or thiobarbituric acid or a barbituric acid derivative or thiobarbituric acid derivative. Another part of the initiator system (c), usually a co-initiator, may be present in the liquid component (A). Preferred components of the initiator system comprise (ii) at least one copper salt or copper complex and (iii) at least one compound having an iogenic halogen atom, particularly preferred is a redox system comprising 1-benzyl-5-phenylbarbituric acid, copper acetylacetonate, triazine derivative, toluidine derivative and/or benzyldibutylammoniumchloride. The afore-mentioned redox systems are suitable as radical initiator systems. In an expedient embodiment, a redox system of this type comprises barbituric acid or thiobarbituric acid, or a barbituric acid or thiobarbituric acid derivative (for example 25 to 80% by weight), at least one copper salt or one copper complex (for example 0.1 to 8% by weight), and at least one compound having an ionogenic halogen atom (for example 0.05 to 7% by weight). Exemplary, suitable ingredients of the afore-mentioned redox system are 1-benzyl-5-phenylbarbituric acid, copper acetylacetonate, copper-II chloride, triazine derivative, toluidine derivative and/or benzyldibutylammoniumchloride.

Preferably, the at least one initiator or the at least one component of the initiator system for autopolymerisation comprises at least one initiator system selected from redox system, comprising oxidising agents and reducing agents selected from barbituric acid or a barbituric acid derivative, sulfinic acid, sulfinic acid derivative or mixtures comprising at least two of the aforementioned reducing agents, particularly preferred is a redox system comprising (i) barbituric acid or thiobarbituric acid or a barbituric acid derivative or thiobarbituric acid derivative or mixtures comprising at least two of the aforementioned reducing agents, preferably in the powdered component, and (ii) at least one copper salt, such as copper-II chloride, or copper complex, and (iii) at least one compound having an ionic halogen atom, in particular (ii) and (iii) are present in the liquid monomer component, particularly preferred is a redox system comprising 1-benzyl-5-phenylbarbituric acid, copper acetylacetonate and triazine derivative, toluidine derivative and/or benzyldibutylammoniumchloride. The toluidine derivative is used as co-initiator for barbituric acid. Optionally, the system (iv) may comprise at least one peroxide. In this case, components (ii) and (ii) are preferably present in the liquid monomer component A and components (i) and optionally (iv) are preferably present in the powdered component.

Preferably, curing of the compositions is made through redox-induced radical polymerisation at room temperature or at slightly elevated temperature, respectively, under a slight pressure in order to avoid the formation of bubbles. A particularly preferred initiator system consists of a combination of barbituric acid in conjunction with copper and chloride ions. This system is characterised by its high level of colour-stability and low toxicity in contrast to peroxide-amine systems.

Furthermore, the powdered component (B) and/or the liquid component (A) may be provided in known manner with further additives from the group of stabilizers, UV-absorbing agents, thixotroping agents and fillers.

The invention is clarified by the examples below, without limiting the invention to these exemplary embodiments.

EXEMPLARY EMBODIMENTS

Production of a powder mixture: A trimodal powder system is produced from three PMMA-based beads together with barbituric acid by mixing. The production of the liquid was made from the components indicated below by mixing.

The measured values below were determined in accordance with norm DIN EN ISO 20795-1. The residual MMA content was also determined in accordance with this norm, analogous to article 8.8. Article 5.2.10 defines that the maximum factor of the stress intensity for materials having heightened impact resistance has to amount to at least 1.9 MPa m$^{1/2}$. The determination is made according to article 8.6. Article 5.2.11 defines that the total fracture work has to amount to at least 900 J/m$^2$. The measurement of the fracture toughness was performed according to article 8.6, analogous to norm EN ISO 20795-1:2013. The device was called: Zwick/Roell Z010, machine type TMT1-FR010TN.A50. In the examples, a core-shell bead, such as the 6681F, was used as fraction having the largest particle diameter, wherein normal beads may also be used. Examples 1-3: All the plastics were produced at the ratio of 10:7 and by means of casting methods. Example 4 was produced at the ratio of 10:5. The determination was made according to article 8.6. The test bodies were polymerised for 30 min at 55° C. and 2 bar pressure.

Example 1

| | % by weight |
|---|---|
| Liquid | |
| MMA | 83.435 |
| aliquat 2-(4,6-diphenyl-1,3,5-triazine-2-yl)-5-((hexyl)oxy)-phenol | 0.15 |
| copper(II) chloride solution | 0.07 |
| UV stabilisers | 0.25 |
| N,N-bis(2(hydroxyethyl)-p-toluidine | 0.1 |
| n-butyl acryloxyethyl carbamate | 10 |
| di-functional, aliphatic urethane acrylate oligomer | 3 |
| tris-(2-hydroxyethyl) isocyanurate triacrylate | 1 |
| styrene-butyl acrylate core-shell particles (200 to 400 nm) | 2 |
| Powder | |
| bead 1 $d_{50}$: 35 μm | 77.56 |
| bead 2 $d_{50}$: 45 μm | 5 |
| bead 3 $d_{50}$ 60 μm | 15 |
| barbituric acid | 2.44 |

In accordance with the usual manner of processing for prosthetic base materials, test bodies were produced according to norm DIN EN ISO 20795-1 (39 mm×8 mm×4 mm) for determination of the physical properties at the ratio powder to liquid of 10:7.

The following measured values were determined:

| | Ex. 1 |
|---|---|
| mechanics 10:7 - flexural strenght [Mpa] | 70.8 |
| mechanics 10:7 I - E-modulus [Mpa] | 2171 |
| mechanics 10:7 - fracture toughness as maximum factor of the stress intensity Kmax [Mpa m$^{1/2}$] | 2.54 |
| mechanics 10:7 I - fracture toughness as total fracture work Wf [J/m$^2$] | 1298 |
| maximum temperature 10:7 [° C.] | 72° C.* |

*measured at RT started polymerisation.

Colour test bodies produced in metal moulds show a transparency of 96%. The residual MMA content, 48 hours after production (standard testing), amounts to 2.0% by weight in the case of a polymerisation time of 30 min, to 1.8% by weight in the case of 60 min. The residual monomer content of MMA, 4 days after production, amounts to 1.8% by weight in the case of a polymerisation time of 30 min.

Example 2

Test bodies are produced analogously to Example 1 in accordance with the composition indicated in the table.

| | % by weight |
|---|---|
| Liquid | |
| MMA | 88.43 |
| aliquat 2-(4,6-diphenyl-1,3,5-triazine-2-yl)-5-((hexyl)oxy)-phenol | 0.15 |
| copper(II) chloride solution | 0.07 |
| UV stabilisers | 0.25 |
| N,N-bis(2(hydroxyethyl)-p-toluidine | 0.1 |
| n-butyl acryloxyethyl carbamate | 5 |

-continued

|  | % by weight |
|---|---|
| di-functional, aliphatic urethane acrylate oligomer | 3 |
| tris-(2-hydroxyethyl) isocyanurate triacrylate | 1 |
| styrene-butyl acrylate core-shell particles | 2 |
| tot. | 100 |
| Powder |  |
| bead 1 $d_{50}$: 35 μm | 67.56 |
| bead 2 $d_{50}$: 45 μm | 15 |
| bead 3 $d_{50}$ 60 μm | 15 |
| barbituric acid | 2.44 |

The following measured values were determined according to the norm stated above (DIN EN ISO 20795-1):

| mechanics 10:7 - flexural strenght [Mpa] | 68.1 |
|---|---|
| mechanics 10:7 I - E-modulus [Mpa] | 2307 |
| mechanics 10:7 - fracture toughness as maximum factor of the stress intensity Kmax [Mpa m$^{1/2}$] | 2.37 |
| mechanics 10:7 I - fracture toughness as total fracture work Wf [J/m$^2$] | 952.7 |
| maximum temperature 10:7 [° C.] | 110.5* |

*measured at RT started polymerisation.

The test bodies show low transparency since the PMMA beads are still visible. The processing time is clearly too short. Even though high-impact properties may be achieved, but the inappropriate mixing of the beads results in an unfavourable temperature profile in which the polymerisation temperatures increases to high, and thus results in losses in processing and transparency.

Example 3

Test bodies are produced analogously to Example 1 in accordance with the composition indicated in the table.

|  | % by weight |
|---|---|
| Liquid |  |
| MMA | 88.43 |
| aliquat 2-(4,6-diphenyl-1,3,5-triazine-2-yl)-5-((hexyl)oxy)-phenol | 0.15 |
| copper(ll) chloride solution | 0.07 |
| UV stabilisers | 0.25 |
| N,N-bis(2(hydroxyethyl)-p-toluidine | 0.1 |
| n-butyl acryloxyethyl carbamate | 20 |
| di-functional, aliphatic urethane acrylate oligomer | 3 |
| tris-(2-hydroxyethyl) isocyanurate triacrylate | 1 |
| styrene-butyl acrylate core-shell particles | 2 |
| tot. | 100 |
| Powder |  |
| bead 1 $d_{50}$: 35 μm | 67.56 |
| bead 2 $d_{50}$: 45 μm | 15 |
| bead 3 $d_{50}$ 60 μm | 15 |
| barbituric acid | 2.44 |

The following measured values were determined:

| mechanics 10:7 - flexural strenght [Mpa] | 61.0 |
|---|---|
| mechanics 10:7 I - E-modulus [Mpa] | 2159 |
| mechanics 10:7 - fracture toughness as maximum factor of the stress intensity Kmax [Mpa m$^{1/2}$] | 1.92 |
| mechanics 10:7 I - fracture toughness as total fracture work Wf [J/m$^2$] | 653.8 |
| maximum temperature 10:7 [° C.] | 66.7° C.* |

*measured at RT started polymerisation.

The samples contain a residual MMA content of 0.9% by weight. However, the high-impact properties are not achieved according to norm mentioned above due to non-ideal conditions in the monomer matrix and bead mixture.

Example 4

The powdered component as well as the liquid component were mixed at the ratio of 10:7 to give the following composition:

| (Ratio 10:7) | % by weight |
|---|---|
| MMA | approx. 34 |
| aliquat 2-(4,6-diphenyl-1,3,5-triazine-2-yl)-5-((hexyl)oxy)-phenol | <1 |
| copper(II) chloride solution | <1 |
| UV stabilisers | <1 |
| N,N-bis(2(hydroxyethyl)-p-toluidine | <1 |
| n-butyl acryloxyethyl carbamate | 4.2 |
| di-functional, aliphatic urethane acrylate oligomer | <2 |
| tris-(2-hydroxyethyl) isocyanurate triacrylate | <1 |
| styrene-butyl acrylate core-shell particles | <1 |
| bead 1 d50: 35 μm | approx. 46 |
| bead 2 d50: 45 μm | 3 |
| bead 3 d50 60 μm | 9 |
| barbituric acid | <2 |
|  | to 100% by weight |

Example 5

The powdered component as well as the liquid component were mixed in the following at the ratio of 10:5 to give the following composition:

| (Ratio 10:5) | % by weight |
|---|---|
| MMA | approx. 28 |
| aliquat 2-(4,6-diphenyl-1,3,5-triazine-2-yl)-5-((hexyl)oxy)-phenol | 0.5 |
| copper(II) chloride solution | <1 |
| UV stabilisers | <1 |
| N,N-bis(2(hydroxyethyl)-p-toluidine | <1 |
| n-butyl acryloxyethyl carbamate | 3.3 |
| di-functional, aliphatic urethane acrylate oligomer | <1 |
| tris-(2-hydroxyethyl) isocyanurate triacrylate | <1 |
| styrene-butyl acrylate core-shell particles | <1 |
| bead 1 $d_{50}$: 35 μm | 52 |
| bead 2 $d_{50}$: 45 μm | 3.3 |
| bead 3 $d_{50}$ 60 μm | 10 |
| barbituric acid | 1.6 |
|  | to 100% by weight |

The polymerised prosthetic material has a total fracture work of 1126.89 J/m$^2$ and a maximum factor of the stress intensity of 2.53 MPa m$^{1/2}$. The E-modulus amounts to 2273 kJ/mol. In order to generate prostheses with optimum fit, the paste mixed at the ratio powder to liquid of 10:5 is injected (into a plaster mould) by means of the injection device Palajet. High-impact values are achieved even with this application method.

The prosthetic materials produced from the monomer mixture according to the invention show a significantly improved fracture toughness over all comparative examples, an increased transparency as well as the least residual monomer content of MMA.

Colour Test Bodies:

The following powder mixtures and monomer mixtures at a ratio of 10 g powder to:7 ml liquid are being vigorously mixed and test bodies with dimensions of 30×30×3 mm are being cast into a metal mould after the swelling phase (approx. 5 min at 23° C.) and being polymerised in Palamat elite for 30 min at 55° C. and 2 bar pressure. The transparency measurements were performed with colorimeter FS600 Datacolor.

Test Bodies for Mechanical Strength:

The following powder mixtures and monomer mixtures at a ratio of 10 g powder to:7 ml liquid are being vigorously mixed and test bodies with dimensions of 100×100×5 mm are being cast after the swelling phase (approx. 5 min at 23° C.) and being polymerised in Palamat elite for 30 min at 55° C. and 2 bar pressure. Subsequently, the test plates are being sawed to the geometry stated in ISO 20795-1 and are being polished. Test bodies for mechanical and colorimetric tests are produced in steel moulds.

The invention claimed is:

1. Autopolymerisable 2-component prosthetic base material comprising the following components:
   A) at least one liquid monomer component,
   B) at least one powdered component,
   wherein
   component (A) comprises
   (i) at least one methyl (meth)acrylate,
   (ii) at least one N-alkyl or N-alkenyl-substituted acryloyloxy carbamate having a molecular mass of less than or equal to 250 g/mol,
   (iii) optionally, at least one at least di-functional urethane (meth)acrylate,
   (iv) at least one di-, tri, tetra- or multi-functional monomer not being urethane (meth)acrylate,
   (v) optionally, polymeric particles having a primary particle size of less than 800 nm,
   (vi) at least one initiator or at least one component of an initiator system for autopolymerisation,
   and component (B) comprises
   (i) at least one powdered component of polymeric particles comprising at least three different fractions of particle sizes of polymeric particles, and
   (ii) at least one initiator or at least one component of an initiator system for autopolymerisation.

2. Prosthetic base material according to claim 1, wherein component (A) comprises
   said polymeric particles (v) present as core-shell particles modified by an elastic phase, and/or component (B) comprises at least one fraction of said polymeric particles (i) present as core-shell particles modified by an elastic phase.

3. Prosthetic base material according to claim 1, wherein an average particle size of each fraction of the at least three different fractions of particle sizes is at least 5 micrometers apart from an average particle size of the other two fractions.

4. Prosthetic base material according to claim 1, wherein component (B) comprises as powdered component polymeric particles with three different fractions, which are selected from 1) polymeric particles of an average particle size of
   a) 25 μm to less than 40 μm,
   b) 40 μm to less than 55 μm,
   c) 55 μm to 100 μm, or
2) polymeric particles of an average particle size of
   a) 35 μm with plus/minus 2.5 μm,
   b) 45 μm with plus/minus 2.5 μm,
   c) 60 μm with plus/minus 2.5 μm,
   wherein a weight ratio of a) to b) to c) is from 12 to 18:1:1 to 5.

5. Prosthetic base material according to claim 1, wherein the N-alkyl- or N-alkenyl-substituted acryloyloxy carbamate is an N-alkyl- or N-alkenyl-substituted acryloyloxy alkylene carbamate.

6. Prosthetic base material according to claim 1, wherein the N-alkyl-substituted acryloyloxy carbamate is n-butyl acryloyloxy ethyl carbamate (BAEC).

7. Prosthetic base material according to claim 1, wherein the polymeric particles (v) comprise core-shell particles, and the primary particle sizes of the core-shell particles are from 500 nm to 10 nm.

8. Prosthetic base material according to claim 1, wherein the at least one initiator or the at least one component of an initiator system for autopolymerisation comprises at least one initiator system selected from (A) a redox system comprising (i) an oxidising agent and (ii) a reducing agent selected from ascorbic acid, ascorbic acid derivative, barbituric acid, barbituric acid derivative, sulfinic acid, sulfinic acid derivative, (B) a redox system comprising (i) barbituric acid or thiobarbituric acid or a barbituric acid derivative or thiobarbituric acid derivative, and (ii) at least one copper salt or one copper complex, and (iii) at least one compound having an ionic halogen atom, and (C) a redox system comprising (i) 1-benzyl-5-phenylbarbituric acid, (ii) copper acetylacetonate and (iii) a triazine derivative, toluidine derivative and/or benzyldibutylammoniumchloride.

9. Prosthetic base material according to claim 1, wherein the prosthetic material comprising components (A) and (B) comprises
   (i) 20 to 50% by weight of methyl methacrylate, and, optionally, at least one 2-alkyl acrylic acid ester not being methyl methacrylate,
   (ii) 1 to 30% by weight of at least one N-alkyl- or N-alkenyl-substituted acryloyloxy carbamate having a molecular mass of less than or equal to 250 g/mol,
   (iii) 0.5 to 10% by weight of at least one at least di-functional urethane (meth)acrylate,
   (iv) 0.05 to 10% by weight of at least one di-, tri-, tetra- or multi-functional monomer not being urethane (meth)acrylate,
   (v) 0.1 to 10% by weight of polymeric particles (v) present as core-shell particles modified by an elastic phase, having a primary particle size of less than 800 nm,
   (vi) 0.05 to 2% by weight of at least one initiator or at least one component of an initiator system for autopolymerisation, and
   (vii) 48.3 to 78.3% by weight of at least one powdered component (i) of polymeric particles comprising at least three different fractions of particle sizes of polymeric particles, wherein the % by weight is based on the total amount of (A) and (B), wherein the three different fractions are selected from polymeric particles of an average particle size of a) 25 µm to less than 40 µm, present at 50 to 90% by weight,
b) 40 µm to less than 55 µm, present at 0.1 to 20% by weight, and
c) 55 µm to 100 µm, present at 0.5 to 30% by weight, wherein the % by weight of a), b) and c) are based on powdered component B.

10. Method for the production of a polymerised prosthetic base material comprising mixing and subsequently polymerizing components:
   A) at least one liquid monomer component, and
   B) at least one powdered component,
   of the prosthetic base material-according to claim 1.

11. Method according to claim 10, which further comprises mixing the liquid monomer component (A) and the powdered component (B) at a weight ratio of 1:10 to 10:1.

12. Polymerised prosthetic base material obtained according to the method of claim 10.

13. Polymerised prosthetic base material according to claim 12, comprising a residual monomer content of methyl methacrylate of less than or equal to 3% by weight determined according to ISO 20795-1:2013, with a total variability of +/−0.05% by weight.

14. Polymerised prosthetic base material according to claim 12, wherein the prosthetic base material has a transparency of greater than or equal to 95% (measured against color test bodies of 3 mm thickness produced in metal molds).

15. Kit comprising an autopolymerisable prosthetic base material, wherein the kit comprises separated components (A) and (B), wherein component (A) comprises
   (i) 60 to 85% by weight of methyl methacrylate,
   (ii) 5 to 20% by weight of at least one N-alkyl- or N-alkenyl-substituted acryloyloxy carbamate having a molecular mass of less than or equal to 250 g/mol,
   (iii) 0.5 to 10% by weight of at least one at least di-function urethane (meth)acrylate,
   (iv) 0.05 to 10% by weight of at least one di-, tri-, tetra- or multi-functional monomer not being urethane (meth)acrylate,
   (v) 0.1 to 10% by weight of polymeric particles (v) present as core-shell particles modified by an elastic phase, having a primary particle size of less than 800 nm,
   (vi) 0.05 to 2% by weight of at least one initiator or at least one component of an initiator system for autopolymerisation, wherein the % by weight of components (i) to (vi) are based on the total amount of component (A), and
   component (B) comprises
   (i) 90 to 99.95% by weight of at least one powdered component of polymeric particles (i) comprising at least three different fractions of particles sizes of polymeric particles, wherein the three different fractions are selected from polymeric particles of an average particle size of
      a) 25 µm to less than 40 µm, present at 50 to 90% by weight,
      b) 40 µm to less than 55 µm, present at 0.1 to 20% by weight, and
      c) 55 µm to 100 µm, present at 0.5 to 30% by weight, and
   (ii) 0.05 to 10% by weight of at least one initiator or at least one component of an initiator system for autopolymerisation, wherein the % by weight of components (i) to (ii) of component B are based on the total amount of component (B).

16. Method of using the prosthetic base material according to claim 1, said method comprising forming the prosthetic base material into a part, wherein the part is selected from dental prostheses, parts of prostheses, occlusal splints, surgical guides for implantology, and mouthguards.

17. Method of using the prosthetic base material according to claim 1, said method comprising cementing a part with the prosthetic base material, wherein the part is selected from artificial articular prostheses, crowns, telescopic prostheses, telescopic crowns, veneers, dental bridges, prosthetic teeth, implants, implant parts, abutments, superstructures, orthodontic appliances, and orthodontic instruments.

18. Method of using the prosthetic base material according to claim 1, said method comprising repairing a hoof of an animal by applying the prosthetic base material to said hoof.

* * * * *